(12) United States Patent
Vinson et al.

(10) Patent No.: US 8,460,640 B2
(45) Date of Patent: Jun. 11, 2013

(54) NARCOTIC DRUG FORMULATIONS WITH DECREASED ABUSE POTENTIAL

(75) Inventors: Robert Vinson, Beaconsfield (CA); Patrick Gosselin, Pierrefonds (CA); Aimesther Ojito Betancourt, Montreal (CA)

(73) Assignee: Paladin Labs, Inc., Montreal, Quebec ( * ) Notice: Subject to any disclaimer, the term of this patent is extended or adjusted under 35 U.S.C. 154(b) by 0 days.

(21) Appl. No.: 13/133,141

(22) PCT Filed: Dec. 14, 2009

(86) PCT No.: PCT/CA2009/001778
§ 371 (c)(1),
(2), (4) Date: Jun. 6, 2011

(87) PCT Pub. No.: WO2010/066034
PCT Pub. Date: Jun. 17, 2010

(65) Prior Publication Data
US 2011/0237615 A1 Sep. 29, 2011

Related U.S. Application Data

(60) Provisional application No. 61/122,117, filed on Dec. 12, 2008.

(51) Int. Cl.
*A61K 49/00* (2006.01)
*A61K 47/00* (2006.01)
*A01N 25/00* (2006.01)

(52) U.S. Cl.
USPC .......................................... 424/10.1; 514/788

(58) Field of Classification Search
None
See application file for complete search history.

(56) References Cited

U.S. PATENT DOCUMENTS

| | | | |
|---|---|---|---|
| 3,885,027 A | 5/1975 | Shaw et al. | |
| 3,980,766 A * | 9/1976 | Shaw et al. | 514/648 |
| 6,228,863 B1 | 5/2001 | Palermo et al. | |
| 6,277,384 B1 | 8/2001 | Kaiko et al. | |
| 6,309,668 B1 | 10/2001 | Bastin et al. | |
| 6,375,957 B1 | 4/2002 | Kaiko et al. | |
| 6,475,494 B2 | 11/2002 | Kaiko et al. | |
| 6,627,635 B2 | 9/2003 | Palermo et al. | |
| 6,663,893 B2 | 12/2003 | Corbo et al. | |
| 6,696,066 B2 | 2/2004 | Kaiko et al. | |
| 6,696,088 B2 | 2/2004 | Oshlack et al. | |
| 6,716,449 B2 | 4/2004 | Oshlack et al. | |
| 7,125,561 B2 | 10/2006 | Sackler | |
| 7,141,250 B2 | 11/2006 | Oshlack et al. | |
| 7,144,587 B2 | 12/2006 | Oshlack et al. | |
| 7,157,103 B2 | 1/2007 | Sackler | |
| 7,172,767 B2 | 2/2007 | Kaiko et al. | |
| 7,201,920 B2 | 4/2007 | Kumar et al. | |
| 7,214,385 B2 | 5/2007 | Gruber | |
| 7,332,182 B2 | 2/2008 | Sackler | |
| 7,384,653 B2 | 6/2008 | Wright, IV et al. | |
| 7,399,488 B2 | 7/2008 | Hirsh et al. | |
| 7,419,686 B2 | 9/2008 | Kaiko et al. | |
| 7,476,402 B2 | 1/2009 | Kumar et al. | |
| 7,510,726 B2 | 3/2009 | Kumar et al. | |
| 7,524,515 B2 | 4/2009 | Roberts | |
| 7,622,441 B2 | 11/2009 | Mickle et al. | |
| 7,655,256 B2 | 2/2010 | Hughes | |
| 7,658,939 B2 | 2/2010 | Oshlack et al. | |
| 7,682,632 B2 | 3/2010 | Oshlack et al. | |
| 7,718,192 B2 | 5/2010 | Oshlack et al. | |
| 7,727,557 B2 | 6/2010 | Sackler | |
| 7,815,934 B2 | 10/2010 | Boehm | |
| 7,842,307 B2 | 11/2010 | Oshlack et al. | |
| 7,842,309 B2 | 11/2010 | Oshlack et al. | |
| 7,842,311 B2 | 11/2010 | Oshlack et al. | |
| 2002/0058673 A1 | 5/2002 | Kaiko et al. | |
| 2002/0106329 A1 | 8/2002 | Leslie | |
| 2002/0187192 A1 | 12/2002 | Joshi et al. | |
| 2003/0004177 A1 | 1/2003 | Kao et al. | |
| 2003/0044458 A1 | 3/2003 | Wright, IV et al. | |
| 2003/0065002 A1 | 4/2003 | Caruso et al. | |
| 2003/0068276 A1 | 4/2003 | Hughes et al. | |
| 2003/0068375 A1 | 4/2003 | Wright et al. | |
| 2003/0091635 A1 | 5/2003 | Baichwal et al. | |
| 2003/0118641 A1 | 6/2003 | Maloney et al. | |
| 2003/0125347 A1 | 7/2003 | Anderson et al. | |
| 2003/0157168 A1 | 8/2003 | Breder et al. | |

(Continued)

FOREIGN PATENT DOCUMENTS

| | | |
|---|---|---|
| CA | 2671197 A1 | 1/2008 |
| WO | WO 2007087452 A2 | 8/2007 |

(Continued)

OTHER PUBLICATIONS

International Search Report, Canadian Intellectual Property Office, regarding International Application No. PCT/CA2009/001778, held in the name of Paladin Labs Inc., mailed on Mar. 10, 2010.

(Continued)

*Primary Examiner* — Jeffrey S. Lundgren
*Assistant Examiner* — Michael Schmitt
(74) *Attorney, Agent, or Firm* — Todd Lorenz; Arnold + Porter LLP

(57) ABSTRACT

The present application relates to novel narcotic formulations having a decreased injection abuse potential In a representative embodiment, the formulation comprises methadone hydrochloride (6-dimethylamino-4,4-diphenylheptan-3-one, a synthetic opiod), meglumine, cellulose, lactose, and magnesium stearate The application further illustrates methods for making the contemplated formulations.

28 Claims, 2 Drawing Sheets

U.S. PATENT DOCUMENTS

| | | |
|---|---|---|
| 2003/0170181 A1 | 9/2003 | Midha |
| 2004/0042964 A1 | 3/2004 | Joshi et al. |
| 2004/0126428 A1 | 7/2004 | Hughes et al. |
| 2004/0228802 A1 | 11/2004 | Chang et al. |
| 2005/0031546 A1 | 2/2005 | Bartholomaus et al. |
| 2005/0163856 A1 | 7/2005 | Maloney et al. |
| 2005/0165038 A1 | 7/2005 | Gordon |
| 2005/0186139 A1 | 8/2005 | Bartholomaus et al. |
| 2005/0191244 A1 | 9/2005 | Bartholomaus et al. |
| 2005/0192309 A1 | 9/2005 | Palermo et al. |
| 2005/0214223 A1 | 9/2005 | Bartholomaus et al. |
| 2005/0236741 A1 | 10/2005 | Arkenau et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0003010 A1 | 1/2006 | Echanagorra et al. |
| 2006/0019872 A1 | 1/2006 | Hong et al. |
| 2006/0034872 A1 | 2/2006 | Woolf |
| 2006/0051298 A1 | 3/2006 | Groenewoud |
| 2006/0058331 A1 | 3/2006 | Galer et al. |
| 2006/0073102 A1 | 4/2006 | Huaihung et al. |
| 2006/0083690 A1 * | 4/2006 | Chang .................. 424/10.2 |
| 2006/0104909 A1 | 5/2006 | Vaghefi et al. |
| 2006/0110327 A1 | 5/2006 | Emigh et al. |
| 2006/0165602 A1 | 7/2006 | Galer et al. |
| 2006/0177380 A1 | 8/2006 | Emigh et al. |
| 2006/0182801 A1 | 8/2006 | Breder et al. |
| 2006/0193782 A1 | 8/2006 | Bartholomaus et al. |
| 2006/0193914 A1 | 8/2006 | Ashworth et al. |
| 2006/0257323 A1 | 11/2006 | Kulli |
| 2007/0003616 A1 | 1/2007 | Arkenau-Maric et al. |
| 2007/0014732 A1 | 1/2007 | Sackler |
| 2007/0020339 A1 | 1/2007 | Bear |
| 2007/0026068 A1 | 2/2007 | Sackler |
| 2007/0048228 A1 | 3/2007 | Arkenau-Maric et al. |
| 2007/0065364 A1 | 3/2007 | Oshlack et al. |
| 2007/0065365 A1 | 3/2007 | Kugelmann et al. |
| 2007/0140975 A1 | 6/2007 | Baichwal et al. |
| 2007/0148097 A1 | 6/2007 | Finn et al. |
| 2007/0148247 A1 | 6/2007 | Joshi et al. |
| 2007/0183979 A1 | 8/2007 | Arkenau-Maric et al. |
| 2007/0183980 A1 | 8/2007 | Arkenau-Maric et al. |
| 2007/0190142 A1 | 8/2007 | Breitenbach et al. |
| 2007/0197451 A1 | 8/2007 | Mickle et al. |
| 2007/0207089 A1 | 9/2007 | Abreu |
| 2007/0224129 A1 | 9/2007 | Guimberteau et al. |
| 2007/0231268 A1 | 10/2007 | Emigh et al. |
| 2007/0243140 A1 | 10/2007 | Giamalua et al. |
| 2007/0269505 A1 | 11/2007 | Flath et al. |
| 2008/0008659 A1 | 1/2008 | Guimberteau et al. |
| 2008/0063725 A1 | 3/2008 | Guimberteau et al. |
| 2008/0069871 A1 | 3/2008 | Vaughn et al. |
| 2008/0069881 A1 | 3/2008 | Caruso et al. |
| 2008/0069891 A1 | 3/2008 | Habib et al. |
| 2008/0075669 A1 | 3/2008 | Soscia et al. |
| 2008/0075768 A1 | 3/2008 | Vaughn et al. |
| 2008/0075770 A1 | 3/2008 | Vaughn et al. |
| 2008/0075771 A1 | 3/2008 | Vaughn et al. |
| 2008/0152595 A1 | 6/2008 | Emigh et al. |
| 2008/0193540 A1 | 8/2008 | Soula et al. |

FOREIGN PATENT DOCUMENTS

| | | |
|---|---|---|
| WO | WO 2008023261 A1 | 2/2008 |
| WO | WO 2008024490 A2 | 2/2008 |
| WO | WO 2008027442 A2 | 3/2008 |
| WO | WO 2008068471 A1 | 6/2008 |

OTHER PUBLICATIONS

Chromy, V., et al., "D(−)-N-Methylglucamine buffer for pH 8.5 to 10.5," Clinical Chemistry, 24(2):379-381 (1978).

Kibbe, A.H., et al., "Monoethanolamine," Handbook of Pharmaceutical Excipients, third edition, pp. 350-351 (2000).

Kibbe, A.H., et al., "Diethanolamine," Handbook of Pharmaceutical Excipients, third edition, pp. 180-181 (2000).

Kibbe, A.H., et al., "Triethanolamine," Handbook of Pharmaceutical Excipients, third edition, pp. 572-573 (2000).

\* cited by examiner

NARCOTIC DRUG FORMULATIONS WITH DECREASED ABUSE POTENTIAL

PRIORITY INFORMATION

The present application claims the benefit of U.S. Provisional Patent Application No. 61/122,117 filed on Dec. 12, 2008, which is hereby incorporated by reference.

FIELD OF THE INVENTION

The present application relates generally to novel drug formulations. In a representative embodiment, the present application relates to new formulations of a pharmaceutically acceptable salt of methadone (6-(Dimethylamino)-4,4-diphenylheptan-3-one, a synthetic opioid) having a decreased abuse potential. The application further includes a method for making this formulation.

BACKGROUND OF THE INVENTION

Drug abusers and/or addicts are known to take a dosage form containing an opioid analgesic, such as oxycodone, morphine or methadone, and crush, shear, grind, chew or dissolve it in water or in alcohol, and either heat it or make it cold in order to subsequently extract the opioid component from the mixture.

The extract, having a significant amount or even an entire amount of the drug, becomes available for immediate absorption by 1) injection, 2) inhalation, or 3) oral consumption.

The use of gel-forming or viscosity increasing agents (e.g. polyvinyl alcohol, HPMC, polyethylene oxide, etc.) to prevent extraction of opioids from solid dosage pharmaceutical preparations is known in the art. In addition, nasal tissue irritants such as sodium lauryl sulfate have been used to deter extraction of active drugs. Alternatively, emetic agents (such as zinc sulfate) as well as pharmaceutical formulations containing an opioid agonist, opioid antagonist or a bittering agent (a bitter chemical used as an aversive agent) have also been evaluated (Kumar et al., 2007, Palermo et al., 2001, Kaiko et al., 2001, Oshlack et al., 2003) to decrease the extractability of drugs such as methadone.

United States Patent Publication 2006/0104909 (Vaghefi et al.) provides examples of abuse-resistant, controlled-release pharmaceutical compositions in which an effective amount of an active compound is wetted with a coating material or distributed throughout a matrix that is insoluble in water and non-erodable at a pH less than about 6. Examples of gel forming polymers or viscosity increasing agents to prevent filtration are known: see, for example, United States Patent Publication No. 2007/0264327 (Acura Pharmaceuticals). Importantly, these examples are used for extended-, controlled- or slow-release pharmaceutical products, where the active pharmaceutical ingredient is released slowly from the composition over an extended period of time (i.e., 8-24 hours).

There remains a need for new formulations that make it difficult, if not impossible, for individuals to extract drugs, such as methadone, from pharmaceutical products in order to reduce the potential for drug abuse. In particular, new formulations are needed which can be used with immediate release pharmaceutical products. Of significant interest are formulations which contain methadone.

New formulations, while having abuse-resistant properties, must allow for the active pharmaceutical ingredient to be soluble in the gastrointestinal tract and have a desired pharmacological activity. In the case of opioids, the pharmacological activity would be an analgesic effect.

SUMMARY OF THE INVENTION

According to one aspect of the present application, an oral pharmaceutical formulation is provided that makes the extraction of an active ingredient more difficult, in particular in aqueous and alcohol solvents, and therefore prevents or at least significantly reduces the potential for abuse, while allowing the pharmaceutical formulation to release the active pharmaceutical ingredient in the gastrointestinal tract upon ingestion to allow for the desired pharmacological effect. The formulation includes a pharmaceutically acceptable salt of a narcotic drug, wherein the narcotic drug has a chemical structure that includes one or more positively charged, protonated amine, and an alkalizing agent.

DETAILED DESCRIPTION

The present application describes formulations which are suitable for many active pharmaceutical ingredients, but is most relevant to narcotic drugs, including but not limited to the opioids oxycodone, morphine, hydromorphone, hydrocodone, and methadone, among others. A physicochemical property required by the active pharmaceutical agent to enable the present invention to confer decreased extractability of the drug is the need for the pharmaceutical agent to be an acidic drug with a chemical structure containing at least one positively charged protonated amine group.

Alkalizing or basifying agents (meglumine, trisodium phosphate ($Na_3PO_4 \cdot 12H_2O$), calcium carbonate ($CaCO_3$), sodium sulfate ($Na_2SO_4$) and sodium bicarbonate ($NaHCO_3$)) reduce or restrain amine or acidic molecule solubility in water. The solubility of an organic compound in aqueous solutions can be altered by the addition of inorganic salts due to a phenomenon called the salting-out effect. Alkalizing agents can be added to compounds having positively charged protonated amines to convert them to their uncharged, free bases, which are less soluble in water than the positively charged protonated amines. Meglumine and trisodium phosphate are strongly alkaline and are used in pharmaceutical formulations as pH adjusting agents. Sodium bicarbonate is also used as a buffer in tablet formulations. Calcium carbonate can alternatively be employed as a pharmaceutical excipient and in this situation is mainly used in solid-dosage forms as a diluent or buffer.

Examples of alkalizing agents which may be used in formulations according to the present application may include meglumine, sodium sulfate, sodium bicarbonate, calcium carbonate, sodium hydroxide, monoethanolamine, diethanolamine, triethanolamine, potassium bicarbonate, potassium citrate, potassium hydroxide, sodium borate, sodium citrate and others with similar physicochemical characteristics generally known in the art.

Oral dosage forms (e.g. tablets, capsules or caplets) combining an opioid such as methadone and an alkalizing agent such as meglumine are manufactured by dry blending and direct compression, in keeping with practices known in the applicable art. Drug formulations according to the present application can be manufactured through dry blending, through aqueous granulation or through dry granulation. The formulation can be in the form of a capsule, caplet, pill, or a compressed tablet. The formulation can be compressed or encapsulated.

Examples of pharmaceutical formulations containing a combination of meglumine are provided below. Other combinations can also be envisaged.

The solubility of methadone hydrochloride in water can be effected by the addition of an alkalizing agent. Table 1, shown below, shows the reduction in solubility of methadone hydrochloride with various alkalizing agents at different molar ratios. The percent reduction in solubility is expressed in comparison to the solubility of methadone hydrochloride without an alkalizing agent.

TABLE 1

Effect of alkalizing agent on the reduction in solubility of methadone hydrochloride in water

| Alkalizing Agent | Methadone/Alkalizing Agent Molar Ratio (mol/mol) | Reduction of Solubility in water (%) |
| --- | --- | --- |
| Meglumine | 0.3 | >90 |
| | 0.6 | >80 |
| | 1.2 | >70 |
| | 1.5 | >60 |
| NaHCO$_3$ | 0.012 | >90 |
| | 0.2 | >30 |
| Na$_2$SO$_4$ | 0.014 | >60 |

According to an embodiment of the present application, an alkalizing agent is used to reduce or impede methadone solubility. Table 2 shows the range of compositions for standard compressible tablets that have been found to be suitable for this purpose. They include standard compressible tablet diluents and disintegrants, fillers, and lubricants, as are generally known in the art.

TABLE 2

Abuse-Resistant Methadone- Alkalizing Agent Formulations

| Ingredient name | wt % range |
| --- | --- |
| Methadone Hydrochloride | 1-5 |
| Alkalizing agent | 0.5-10 |
| Compressible tablet diluent and disintegrant | 20-80 |
| Compressible tablet filler | 20-80 |
| Tablet lubricant | 0.1-5 |

When the solid formulation of Table 2 is crushed or dispersed into an aqueous solution, the presence of the alkalizing agent significantly reduces methadone solubility. Therefore, methadone precipitates along with other ingredients out of the solution and is retained e.g. on standard filters used to prepare a solution for illicit drug use, for instance intravenous injection. In a 1 gram tablet, there can be 0.029-0.14 mmols of methadone hydrochloride (molecular weight=345.9) and 0.26-1.2 mmols of alkalizing agent, depending on which alkalizing agent is chosen (molecular weight ranging from, for example, 84.0 for NaHCO$_3$ to 195.2 for meglumine).

Table 3 illustrates meglumine-based formulations according to an aspect of the present application. These formulations include standard compressible tablet diluents and disintegrants, fillers and lubricants, as are known generally in the art.

TABLE 3

Abuse-Resistant Methadone-Meglumine Formulations

| Ingredient name | wt % range |
| --- | --- |
| Methadone Hydrochloride | 1-5 |
| Meglumine | 0.5-10 |
| Compressible tablet diluent and disintegrant | 20-80 |
| Compressible tablet filler | 20-80 |
| Tablet lubricant | 0.1-5 |

Table 4 shows a particular embodiment of a tablet formulation according to the present application. A pharmaceutically-acceptable colorant, as well as a protective coating, may be added to the formulation.

TABLE 4

Abuse-Resistant Methadone-Meglumine Formulations

| Ingredient name | wt % range |
| --- | --- |
| Methadone Hydrochloride | 1-5 |
| Meglumine | 0.5-10 |
| Cellulose | 20-80 |
| Lactose | 20-80 |
| Magnesium Stearate | 0.1-5 |
| Colorant | 0.01-5 |

Tablets as per the embodiments listed in Tables 2-4 containing various amounts of meglumine along with selected standard directly compressible excipients were prepared. Tablets were then crushed using a mortar/pestle. The powder was transferred into a glass vial and diluted in the extraction solvent. The solutions were then submitted to different treatments: 1) heating at 100° C., 2) cooling under 0° C. and 4) magnetic stirring at 1100 rpm. The solutions were filtered using 5 mL BD syringe filter nylon membrane (pore size 0.45 μm) and evaluated for the release of methadone into the extraction solvent.

Formulations with methadone alone (Example 1) demonstrated that over 60% of the methadone could be extracted using water as a solvent; the addition of the non-meglumine components shown in Table 4 allowed for slightly less methadone recovery in various alcohol solutions. The addition of meglumine, as in Examples 2-6 described below, decreased methadone extraction with water to less than 20% of the total methadone available in the tablet formulation. In addition, decreased solubility in alcohol solutions of up to 95% was seen in formulations containing alkalizing agents.

Modifications and variations can be effected to the particular embodiments by those of skill in the art without departing from the scope of the attached claims.

Dissolution tests are used to determine how a drug is released from solid oral pharmaceutical preparations, such as tablets and capsules. This testing is done to ensure that the drug is released from the oral preparation, and should generally be dissolved in the fluid of the gastrointestinal (GI) tract to allow desired pharmacological effect. Indeed dissolution of the drug in physiological fluids is required for absorption of the drug from the GI tract into the blood circulation to exert its desired physiological effect.

Several dissolution solutions or media can be used to simulate dissolution in the gastrointestinal tract. These include Simulated Gastric Fluid (SGF) and 0.1N hydrochloric acid (HCL), among others.

As shown in FIG. 1, meglumine containing formulations demonstrated rapid dissolution in acidic simulated gastric fluid media. However, these formulations impeded methadone solubility/dissolution in water media compared to a formulation that did not contain meglumine (FIG. 2). These results demonstrate that the abuse-resistant properties of the use of alkalizing agents with or without polymers as described in this application does not impede with the physiological dissolution of the drug product in simulated physiological gastrointestinal tract fluid.

EXAMPLES

Figure 1:
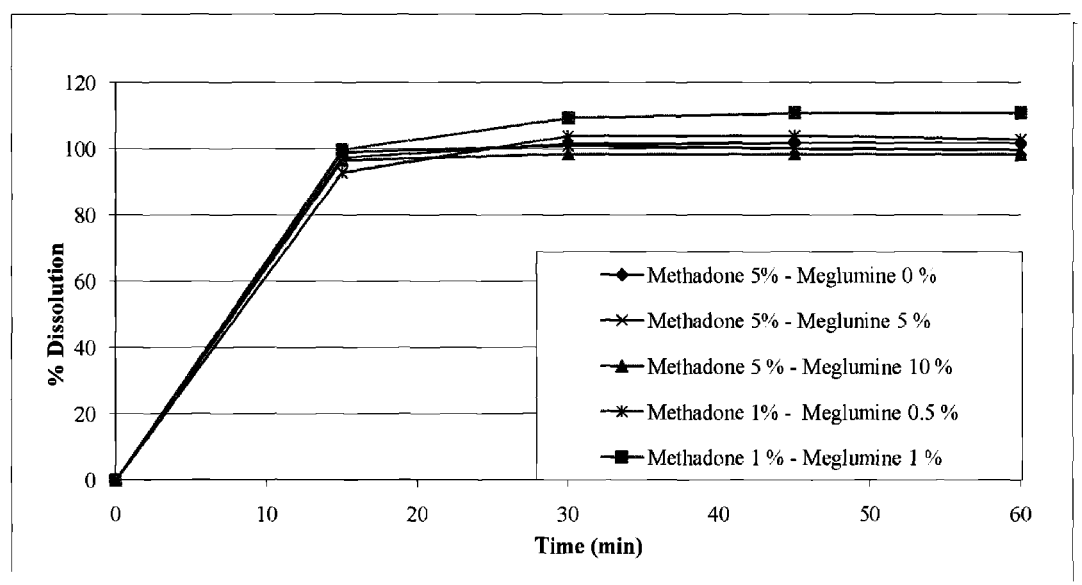
FIG. 1: Comparative dissolution profiles of methadone formulations in simulated gastric media (SGF) with various combinations of methadone and meglumine.
Figure 2:
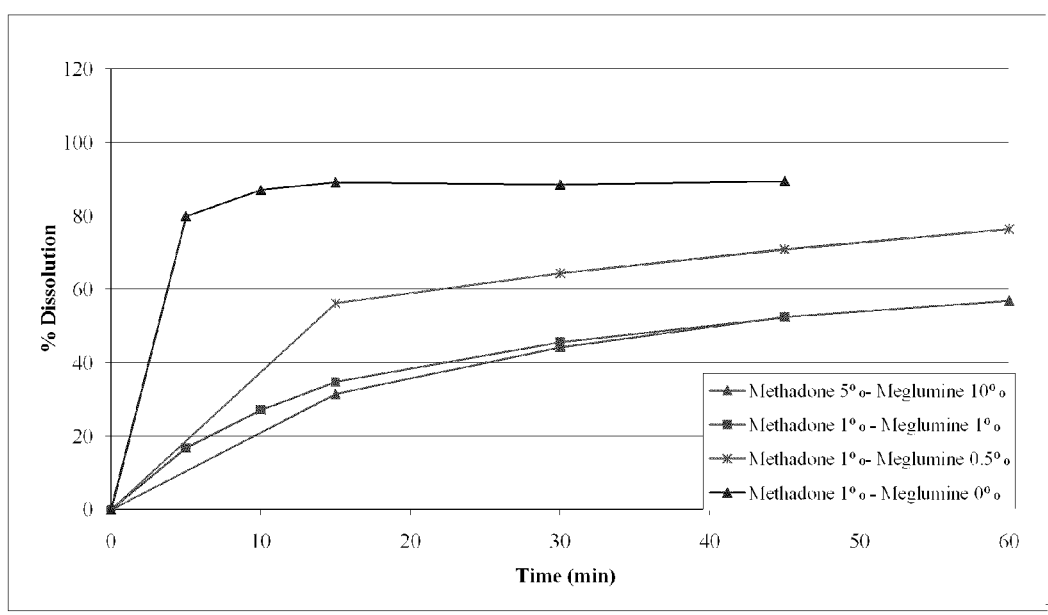
FIG. 2: Comparative dissolution profiles of methadone formulations in water with various combinations of methadone and meglumine.

The following examples provide specific pharmaceutical compositions using the present invention; however, the scope of the invention is not limited to these examples.

Example 1

Preparation of Tablets Containing Methadone

All ingredients were first sieved on 30 mesh sieve. Lactose (1.5 grams) and methadone (0.1 grams) were mixed in a V-blender for about 5 minutes at 25 RPM. Microcrystalline cellulose (4.3 grams) and lactose (2.9 grams) were combined separately in a V-blender, blended for about 2 minutes at 25 RPM. The two mixtures were then combined. FD&C blue dye (0.003 grams) was added to microcrystalline cellulose (1.2 grams) in a V-blender and mixed for about 2 minutes at 25 RPM. This mix was added to the previously combined mixture, mixed in the V-Blender for 15 minutes at 25 RPM, and then magnesium stearate (0.1 grams) was added, and mixed for around 2 minutes at 25 RPM. This final mixture was then used to create tablets (tablet weight: 100 mg) via direct compression using a hydraulic press with 8 mm diameter die in combination with standard concave upper and lower punches.

Example 2

Preparation of Tablets Containing Methadone and 1 Wt % Meglumine in a Mol Ratio of 0.6 (Methadone/Meglumine)

All ingredients were first sieved on 30 mesh sieve. Lactose (1.4 grams), meglumine (0.1 grams) and methadone (0.1 grams) were mixed in a V-blender for about 5 minutes at 25 RPM. Microcrystalline cellulose (4.3 grams) and lactose (2.9 grams) were combined separately in a V-blender, blended for about 2 minutes at 25 RPM. The two mixtures were then combined. FD&C blue dye (0.03 grams) was added to microcrystalline cellulose (1.2 grams) in a V-blender and mixed for about 2 minutes at 25 RPM. This mix was added to the previously combined mixture, mixed in the V-Blender for 15 minutes at 25 RPM, and then magnesium stearate (0.1 grams) was added, and mixed for around 2 minutes at 25 RPM. This final mixture was then used to create tablets (tablet weight: 100 mg) via direct compression using a hydraulic press with 8 mm diameter die in combination with standard concave upper and lower punches.

Example 3

Preparation of Tablets Containing Methadone and 2 Wt % Meglumine in a Mol Ratio of 1.4 (Methadone/Meglumine)

All ingredients were first sieved on 30 mesh sieve. Lactose (14.0 grams), meglumine (2.0 grams) and methadone (5.0 grams) were mixed in a V-blender for about 5 minutes at 25 RPM. Microcrystalline cellulose (18.0 grams) and lactose (28.0 grams) were combined separately in a V-blender, blended for about 2 minutes at 25 RPM. The two mixtures were then combined. Microcrystalline cellulose (32.0 grams) was added to the previously combined mixture, mixed in the V-Blender for 15 minutes at 25 RPM, and then magnesium stearate (1.0 grams) was added, and mixed for around 2 minutes at 25 RPM. This final mixture was then used to create tablets (tablet weight: 500 mg) via direct compression using a hydraulic press with 10 mm diameter die in combination with standard concave upper and lower punches.

Example 4

Preparation of Tablets Containing Methadone and 0.5 Wt % Meglumine in a Mol Ratio of 1.1 (Methadone/Meglumine)

All ingredients were first sieved on 30 mesh sieve. Lactose (1.1 grams), meglumine (0.025 grams) and methadone (0.05 grams) were mixed in a V-blender for about 5 minutes at 25 RPM. Microcrystalline cellulose (1.0 grams) and lactose (1.1 grams) were combined separately in a V-blender, blended for about 2 minutes at 25 RPM. The two mixtures were then combined. FD&C blue dye (0.002 grams) was added to microcrystalline cellulose (1.7 grams) in a V-blender and mixed for about 2 minutes at 25 RPM. This mix was added to the previously combined mixture, mixed in the V-Blender for 15 minutes at 25 RPM, and then magnesium stearate (0.05 grams) was added, and mixed for around 2 minutes at 25 RPM. This final mixture was then used to create tablets (tablet weight: 100 mg) via direct compression using a hydraulic press with 8 mm diameter die in combination with standard concave upper and lower punches.

Example 5

Preparation of Tablets Containing Methadone and 5 Wt % Meglumine in a Mol Ratio of 0.6 (Methadone/Meglumine)

All ingredients were first sieved on 30 mesh sieve. Lactose (1.0 grams), meglumine (0.3 grams) and methadone (0.3 grams) were mixed in a V-blender for about 5 minutes at 25 RPM. Microcrystalline cellulose (1.5 grams) and lactose (1.5 grams) were combined separately in a V-blender, blended for about 2 minutes at 25 RPM. The two mixtures were then combined. Microcrystalline cellulose (1.5 grams) was added to the previously combined mixture, mixed in the V-Blender for 15 minutes at 25 RPM, and then magnesium stearate (0.06 grams) was added, and mixed for around 2 minutes at 25 RPM. This final mixture was then used to create tablets (tablet weight: 200 mg) via direct compression using a hydraulic press with 8 mm diameter die in combination with standard concave upper and lower punches.

Example 6

Preparation of Tablets Containing Methadone and 10 Wt % Meglumine in a Mol Ratio of 0.3 (Methadone/Meglumine)

All ingredients were first sieved on 30 mesh sieve. Lactose (1.0 grams), meglumine (0.6 grams) and methadone (0.3 grams) were mixed in a V-blender for about 5 minutes at 25 RPM. Microcrystalline cellulose (1.4 grams) and lactose (1.3 grams) were combined separately in a V-blender, blended for about 2 minutes at 25 RPM. The two mixtures were then combined. Microcrystalline cellulose (1.4 grams) was added to the previously combined mixture, mixed in the V-Blender for 15 minutes at 25 RPM, and then magnesium stearate (0.06 grams) was added, and mixed for around 2 minutes at 25 RPM. This final mixture was then used to create tablets (tablet weight: 200 mg) via direct compression using a hydraulic press with 8 mm diameter die in combination with standard concave upper and lower punches.

The above-described embodiments of the present application are intended to be examples only. Variations, alterations and modifications can be made to the particular embodiments described herein by those of skill in the art without departing from the scope of the appended claims.

The invention claimed is:

1. An oral drug formulation for reducing potential for abuse, the formulation comprising: a pharmaceutically acceptable salt of a narcotic drug, wherein the narcotic drug has a chemical structure that includes at least one positively charged protonated amine; and an alkalizing agent for reducing the solubility of the narcotic drug in a non-acidic solution, wherein the alkalizing agent comprises an amine containing compound selected from the group consisting of meglumine, monoethanolamine, diethanolamine and triethanolamine; wherein the alkalizing agent is present in a molar ratio between 0.1 and 1.5 mol of the positively charged protonated amine/mol alkalizing agent.

2. The drug formulation as defined in claim 1, wherein said narcotic drug is an opioid.

3. The drug formulation as defined in claim 2, wherein said opioid is selected from the group consisting of oxycodone, morphine, hydromorphone, hydrocodone, oxymorphone, codeine, and methadone.

4. The drug formulation as defined in claim 1, wherein said alkalizing agent is meglumine.

5. The drug formulation as defined in claim 4, wherein the narcotic drug and meglumine are present in a molar ratio of less than 1.5 mol narcotic drug/mol meglumine.

6. The drug formulation as defined in claim 5, wherein the narcotic drug is methadone.

7. The drug formulation as defined in claim 1, further comprising one or more of the following: a compressible tablet diluent and disintegrant, a compressible tablet filler, a tablet lubricant and a colorant.

8. The drug formulation as defined in claim 7, wherein: the pharmaceutically acceptable salt of the narcotic drug is methadone hydrochloride, and the methadone hydrochloride is present in an amount between 1-30 wt %, the alkalizing agent is present in an amount between 0.5-30 wt %, the compressible tablet diluent and disintegrant is present in an amount between 20-80 wt %, the compressible tablet filler is present in an amount between 20-80 wt % and the tablet lubricant is present in an amount between 0.1-5 wt %.

9. The drug formulation as defined in claim 8, wherein: the methadone hydrochloride is present in an amount between 1-5 wt %, and the alkalizing agent is present in an amount between 0.5-10 wt %.

10. The drug formulation as defined in claim 8, wherein the alkalizing agent is meglumine.

11. The drug formulation as defined in claim 1 comprising methadone hydrochloride and meglumine, wherein methadone extraction with water is less than about 10% of the total methadone available in tablet form.

12. The drug formulation as defined in claim 1 comprising methadone hydrochloride and meglumine, wherein methadone extraction in alcoholic solutions is less than about 50% of the total methadone available in tablet form.

13. The drug formulation as defined in claim 11, wherein the methadone hydrochloride is present in an amount between 1-30 wt %, the meglumine is present in an amount between 0.5-30 wt %, a compressible tablet diluent and disintegrant is present in an amount between 20-80 wt %, a compressible tablet filler is present in an amount between 20-80 wt % and a tablet lubricant is present in an amount between 0.1-5 wt %.

14. The drug formulation as defined in claim 13, wherein the methadone hydrochloride is present in an amount between 1-5 wt %, the alkalizing agent is present in an amount between 0.5-10 wt %.

15. The drug formulation as defined in claim 11 wherein more than 70 wt % of the methadone hydrochloride dissolves in 15 minutes in USP simulated gastric fluid.

16. The drug formulation as defined in claim 11 having an in vitro dissolution rate of the methadone hydrochloride, when measured with USP apparatus Type II at 100 rpm in USP simulated gastric fluid, between about 5 wt % and about 30 wt % after 5 minutes; between about 40 wt % and about 80 wt % after 10 minutes; or between about 70 wt % and about 100 wt % after 15 minutes.

17. The drug formulation as defined in claim 1 comprising methadone hydrochloride and meglumine, wherein, when the formulation is crushed and exposed to small volume of water with stirring for 5 minutes at room temperature, less than about 5% by weight of the pharmaceutically active agent originally present in the formulation before it was crushed is released into the water.

18. The drug formulation as defined in claim 1 comprising meglumine, wherein, when the formulation is crushed and exposed to a small volume of solution containing 95% (v/v) ethanol with stirring for 5 minutes at room temperature, less than about 50% by weight of the pharmaceutically active agent originally present in the formulation before it was crushed is released into the aqueous solution.

19. A process for manufacturing a drug formulation as defined in claim 1, which process includes a step of combining the constituents of the drug formulation through dry blending, aqueous granulation, or dry granulation, wherein the formulation is in the form of a capsule, caplet, pill or a compressed tablet.

20. The drug formulation as defined in claim 9, wherein the alkalizing agent is meglumine.

21. The drug formulation as defined in claim 12, wherein the methadone hydrochloride is present in an amount between 1-30 wt %, the meglumine is present in an amount between 0.5-30 wt %, a compressible tablet diluent and disintegrant is present in an amount between 20-80 wt %, a compressible tablet filler is present in an amount between 20-80 wt % and a tablet lubricant is present in an amount between 0.1-5 wt %.

22. The drug formulation as defined in claim 21, wherein the methadone hydrochloride is present in an amount between 1-5 wt %, the alkalizing agent is present in an amount between 0.5-10 wt %.

23. The drug formulation as defined in claim 12 wherein more than 70 wt % of the methadone hydrochloride dissolves in 15 minutes in USP simulated gastric fluid.

24. The drug formulation as defined in claim 12 having an in vitro dissolution rate of the methadone hydrochloride, when measured with USP apparatus Type II at 100 rpm in USP simulated gastric fluid, between about 5 wt % and about 30 wt % after 5 minutes; between about 40 wt % and about 80 wt % after 10 minutes; or between about 70 wt % and about 100 wt % after 15 minutes.

25. A method for reducing potential for abuse of a narcotic drug, the method comprising: providing to a patient an oral formulation of the drug, wherein the formulation comprises: a pharmaceutically acceptable salt of the narcotic drug comprising a chemical structure that includes at least one positively charged protonated amine; and an alkalizing agent for reducing the solubility of the narcotic drug in a non-acidic solution, the alkalizing agent comprising: an amine containing compound selected from the group consisting of meglumine, monoethanolamine, diethanolamine and triethanolamine; wherein the alkalizing agent is present in a molar ratio between 0.1 and 1.5 mol of the positively charged protonated amine/mol alkalizing agent.

26. The method according to claim 25, wherein the narcotic drug is methadone.

27. The method according to claim 25, wherein the alkalizing agent is meglumine.

28. The method according to claim 25, wherein the pharmaceutically acceptable salt of the narcotic drug is methadone hydrochloride and the alkalizing agent is meglumine, and wherein:
- a) methadone extraction with water is less than about 10% of the total methadone available in tablet form;
- b) methadone extraction in alcoholic solutions is less than about 50% of the total methadone available in tablet form;
- c) more than 70 wt % of the methadone hydrochloride dissolves in 15 minutes in USP simulated gastric fluid;
- d) the drug formulation has an in vitro dissolution rate of the methadone hydrochloride, when measured with USP apparatus Type II at 100 rpm in USP simulated gastric fluid, between about 5 wt % and about 30 wt % after 5 minutes; between about 40 wt % and about 80 wt % after 10 minutes; or between about 70 wt % and about 100 wt % after 15 minutes;
- e) when the drug formulation is crushed and exposed to small volume of water with stirring for 5 minutes at room temperature, less than about 5% by weight of the methadone originally present in the formulation before it was crushed is released into the water; and/or
- f) when the formulation is crushed and exposed to a small volume of solution containing 95% (v/v) ethanol with stirring for 5 minutes at room temperature, less than about 50% by weight of the pharmaceutically active agent originally present in the formulation before it was crushed is released into the aqueous solution.

* * * * *